United States Patent [19]

Eibl et al.

[11] Patent Number: 5,827,818
[45] Date of Patent: Oct. 27, 1998

[54] AGENT FOR SUBCUTANEOUS ADMINISTRATION OF PROTEIN C

[75] Inventors: Johann Eibl; Hans-Peter Schwarz, both of Vienna, Austria

[73] Assignee: Immuno Aktiengesellschaft, Vienna, Austria

[21] Appl. No.: 617,365

[22] Filed: Mar. 20, 1996

[30] Foreign Application Priority Data

Mar. 21, 1995 [DE] Germany ............... 195 10 260.6
Mar. 4, 1996 [DE] Germany ............... 196 08 218.8

[51] Int. Cl.⁶ ................................. A61K 37/00
[52] U.S. Cl. ................................. 514/2; 514/21
[58] Field of Search .......................... 514/2, 21

[56] References Cited

U.S. PATENT DOCUMENTS 5,279,956 1/1994 Griffin et al. .
5,358,932 10/1994 Foster et al. .

FOREIGN PATENT DOCUMENTS

0471660A2 2/1992 European Pat. Off. .
0471660A3 2/1992 European Pat. Off. .
0514367A2 11/1992 European Pat. Off. .
0519900A1 12/1992 European Pat. Off. .
0519903A1 12/1992 European Pat. Off. .
0533210A1 3/1993 European Pat. Off. .

OTHER PUBLICATIONS

Embase Abstract 93038768 (1992). Samama et al.
Okajima et al., Thrombosis and Haemostatis 63(1): 48–53 (1990).
Gruber et al. Blood 73(3): 639–642 (Feb. 15, 1989).
Taylor et al., J. Clin. Invest., 79: 918–925 (Mar. 1987).
Reynolds Martindale, The Extra Pharmacopoeia, pp. 647–648 (1993).
Yan et al. Prespectives in Drug Discovery & Design, 1: 503–520 (1993).
Schwarz et al. Advances in Applied Biotechnology Series 2: 83–89 (1990).
Mitchell et al. Pediatric Research 37(4), Abstract 916, p. 163A (Apr. 1995).
Samama et al. Jeur. 5: 213–217 (1992) (abstract already of record).

*Primary Examiner*—Zohrem Fay
*Attorney, Agent, or Firm*—Foley & Lardner

[57] ABSTRACT

The invention relates to a pharmaceutical agent which is suitable for subcutaneous injection of protein C, wherein it comprises protein C and a pharmaceutically acceptable carrier.

26 Claims, No Drawings

AGENT FOR SUBCUTANEOUS ADMINISTRATION OF PROTEIN C

The invention relates to a pharmaceutical agent which is suitable for subcutaneous injection of protein C.

BACKGROUND OF THE INVENTION

Protein C is synthesized in the liver and circulates in blood as an inactive, two-chained protein or zymogen in a concentration of 4 µg/ml. In the activation by thrombin-thrombomodulin complex on the surface of the vessel wall endothelium, the activation peptide of protein C is cleaved at the N-terminal end of the heavy chain of the zymogen, and activated protein C, a serine protease, is formed.

Protein C can be purified from plasma or a plasma fraction such as from coagulation factor concentrate, also called prothrombin complex, and optionally activated in vitro. The product obtained thereby can be contaminated by viruses found in blood and frequently present in plasma. For this reason, a series of steps are carried out during the production process in order to inactivate or eliminate viruses.

Recently, protein C and its activated forms, derivatives and mutants thereof has been produced with the aid of recombinant DNA technology.

Patients that suffer from a deficiency of protein C frequently show thrombo-embolic complications such as a purpura fulminans-like syndrome. Purpura fulminans in newborn, homozygote children with protein C deficiency could be successfully treated with a highly purified protein C concentrate. The treatment began with a dose of 20 to 40 units/kg, four times daily. The therapy was performed over 8 months with 100 U/kg/day (H. P. Schwarz et al., Blood, Vol., No. 10, Nov. 15, 1990, Suppl. 1, Abstract 2070, page 520a).

In its activated form, Protein C has an anticoagulant action in the proteolytic digestion of coagulation Factor Va, the cofactor for Factor Xa induced prothrombin activation (thrombin formation) and factor VIIIa, the cofactor for Factor IXa induced Factor X activation.

It is described in the literature that activated protein C (APC) prevents endotoxin induced sepsis and septic shock in a baboon animal experiment (Taylor et al., J. Clin. Invest., volume 79, March 1987, pp. 918–925). A further use of activated protein C results from its antithrombotic function which was noted by Gruber et al. (Blood, volume 73, No. 3, Feb. 15, 1989, pp. 639–642).

It is suggested by these authors that APC administration under arterial flow conditions can immediately lead to antithrombotic effects.

Activated protein C itself also leads to thrombolysis in animal experiments with rats (EP- 0 519 903). Thereby, it is important that the thrombolytic preparation of activated protein C contains no impurities, such as viral contamination or thrombin and serum amyloid P, which could either arise from the starting material or from the production process.

Surprisingly, it has been shown that protein C zymogen is also suitable for thrombolysis treatment (EP-0 519 900). It was determined that protein C deficiency is caused by plasmin, the active enzyme of fibrinolysis. This deficiency manifests itself in that the coagulation and fibrinolysis systems are not balanced which leads to formation of thrombi and reocclusion. Protein C remedies this deficiency state and therewith improves the thrombolysis therapy.

By means of a previously unknown mechanism, protein C zymogen is also capable of improving microcirculation and treating and preventing clinical equivalents of the Shwartzman reaction (EP- 0 514 367).

Additionally, a substantially broader applicability of protein C resulted from the experiments. It was unexpectedly established that pain reactions, inflammations and vessel damage in a carageenin induced rat paw model of hyperanalgesia are inhibited by protein C (EP- 0 533 210).

Protein C or activated protein C was previously administered intravenously to patients, either prophylactically or in thrombo-embolic complications, to obtain immediate effect. Okajima et al. (Thrombosis and Haemostasis, 1990, volume 63(1), pp. 48–53) intravenously injected activated protein C in a dose of 24 µg/kg and non-activated protein C in a dose of 0.15 mg/kg. They determined that the half-life for APC is 23 minutes and is 10.9 hours for protein C as determined by the prolongation of the activated partial thromboplastin time.

For this reason it is often necessary to administer high doses or carry out frequent administrations of protein C and/or activated protein C. Although some derivatives of protein C or activated protein C possess an increased half-life in vivo, the administration of protein C or activated protein C still represents an encumbrance for patients as a result of the long infusion times.

The repeated use of intravenous injections is not only time-consuming for patients, it also leads to side effects. A series of anaphylactic reactions can result from intravenous injection. Above all, an occlusion and/or thrombic state and also infection of the vein or venous entries (catheter, implanted catheter such as PORT-A-CAT®) at the site of injection can result from long-term treatments. Thereby, life threatening conditions such as embolisms, especially pulmonary embolisms, can occur. In patients with small veins such as babies it is additionally difficult for the doctor to introduce the needle into the vein.

An object of the present invention is to make available new pharmaceutical agents which permit easy and uncomplicated administration of protein C.

SUMMARY OF THE INVENTION

The above object is solved by pharmaceutical agents which are suitable for subcutaneous administration of protein C. Thereby, protein C can be present as a zymogen or in its activated form, as native protein C, as a derivative or mutant. Native protein C is according to definition of natural origin and is contained for example in plasma or a plasma fraction such as prothrombin complex. However, an analogous native protein C can also be produced from appropriate cell cultures and/or constitute a recombinant protein. The agent to be used for subcutaneous injection comprises protein C and a pharmaceutically acceptable carrier and is suitable for administration of an effective dose of protein C to patients with protein C deficiency.

In accordance with another aspect of the present invention, there are provided methods of administering agents containing protein C to a patient, comprising the step of subcutaneously injecting the patient with an agent comprising protein C and a pharmaceutically acceptable carrier. The protein C can be from natural or recombinant sources, and can be in the zymogen and/or activated form and is preferably native protein C. Preferably, the protein C is at least 80% pure, and more preferably is at least 90% pure. The protein C to be administered is preferably treated to inactivate, reduce, remove or eliminate contaminating pathogens, such as viruses. Kits to facilitate subcutaneous injection also are provided.

In accordance with still another aspect of the present invention, agents containing protein C can be administered intramuscularly. The protein C can be in the same or similar form as that used for subcutaneous injection. Kits to facilitate intramuscular injection also are provided.

These and other aspects of the present invention will become apparent to those of skill in the art in view of the teachings contained herein.

DETAILED DESCRIPTION OF PREFERRED EMBODIMENTS

It has surprisingly emerged that even native protein C is suitable for subcutaneous injection. Essential for this is the unexpectedly fast recovery of therapeutic amounts of protein C in blood of patients after subcutaneous injection. Therefore, despite an unaltered short half-time of native protein C, the effective increase of the protein C concentration in blood is possible.

Above all, this was surprising in view of the prior art (U.S. Pat. No. 5,358,932) which proposes modified protein C molecules with an elongated half-life in order to prevent the problem of the relative short half-life of native protein C.

The preferred daily dose lies in the range of 5 to 500 U/kg, most preferably between 10 and 200 U/kg. The effective amount of protein C is dependent on the protein C concentration in the blood of patients and the protein C concentration as it is required for prophylaxis or therapy. The preferred minimum concentration of protein C in the solution which is ready to be administered is 200 U/kg, most preferably a concentration in the range of 250 to 1000 U/kg. In contrast to the preparations of the prior art which are administered intravenously, the volume of the agent according to the invention is generally small and is about 1 to 10 ml. It is preferred to inject considerably concentrated protein C solutions.

Small volumes are preferably made available as solutions which are ready to be administered in complete syringes. The syringes for subcutaneous administration of protein C has particularly thin, relatively long needles. The liquid preparation which is ready to be administered is preferably stabilized and storable at refrigerator temperature over a time period of several weeks. As stabilizers, amino acids, sugars, but also tensides and above all non-ionic tensides such as Tween or Triton are used for example. Polyalkylene glycols such as for example polyethylene glycol are also suitable substances for the stabilization of protein C.

A liquid, deep-frozen protein C preparation in a syringe for subcutaneous injection can also be made available.

In using lyophilized protein C preparations, the cold chain must not necessarily be adhered to. A kit relating to this comprises a container with lyophilized protein C and a syringe which is suitable for subcutaneous injection of protein C. Appropriate instructions are then given in the product information sheet for dissolution of the preparation in water for injection or buffer and/or a stabilizing solution.

Larger amounts of protein C solution can be administered for example with appropriate pumps over a time period of 10 min. to approximately 5 hours. As an alternative to subcutaneous administration of protein C, the agent can be administered intramuscularly.

Protein C can be administered as a prothrombin complex which comprises protein C or as highly purified protein C concentrate which is at least 80%, preferably at least 90% (w/w) pure, in relationship to the total protein. Advantageously, the agent according to the invention additionally comprises cofactors of protein C, for example, protein S and/or the anticoagulation-active Factor V.

The agent according to the invention comprises protein C which is isolated from a biological source such as blood, plasma or a plasma fraction and is preferably treated for inactivation of a virus which may possibly be present. The agent can also be produced with the aid of a recombinant method.

The agent according to the invention is particularly suitable in methods for treating patients that suffer among a number of the disease states described above, wherein it is prophylactically or therapeutically administered. Inherited or acquired protein C deficiencies are among the medical indications to be named. In each case, the content of protein C or activated protein C in blood is adjusted to normal, and even above normal concentrations (from 70 to 200, preferably 100%).

The required dose in the administration of activated protein C is approximately 1/10 the amount given for the zymogen. With simultaneous use of cofactors and/or agonists, a correspondingly smaller dose of protein C can suffice.

Surprisingly, it could be shown in rabbit experiments that even a single subcutaneous (sc) injection of a protein C concentrate with a dose in the range of 100 to 1000 μg/kg could maintain the therapeutic level up to 100 hours. Depending on the administered protein C dose, this state can even be maintained over a longer time period by higher protein C doses. In this manner, it is possible, for example, to administer a subcutaneous injection twice a week to patients suffering from protein C deficiency, and thereby, to maintain the required level of protein C. This is preferable to intravenous injection because patients can treat themselves at home in this manner.

It was not to be expected that protein C is already found in the circulatory system a short time after subcutaneous injection. Rather, it was assumed that the major part of the protein C would be degraded as a result of the relatively short half-life. Surprisingly, it became apparent that therapeutic amounts of protein C are already found in the blood of mammals approximately 30 min. after the administration of protein C.

The advantage of the administration according to the invention is to be found above all in the fact that the agent introduces protein C into the circulatory system over a long time period. Through the subcutaneous injection, a corresponding depot results from which a continuous release of the substances into the circulatory system occurs. Therewith, the problem of continuous administration of protein C, which is required based on the limited half-life in blood, is overcome.

The subcutaneously injected protein C is then present in blood in non-modified form. No activation of protein C zymogen occurs through subcutaneous administration.

The following non-limiting Examples serve to more closely illustrate the invention.

EXAMPLE 1

Subcutaneous administration of protein C to a rabbit $^{125}$I radioactive labeled protein C was administered subcutaneously to a rabbit (200 μl/ at a concentration of 0.16 μg/ml). At specific time intervals after the administration blood samples were taken. Plasma from these blood samples was separated with SDS-PAGE and the labeled protein C was detected with x-ray film. A quantity of labeled protein C in non-degraded form was already found in the blood after 30 minutes and was constantly high over the observation time period of 180 minutes.

EXAMPLE 2

Subcutaneous administration of protein C to a patient

A patient with severe inherited protein C deficiency was treated with 1500 units of protein C in a volume of 20 ml over 2 hours. The administration occurred subcutaneously in the skin of the abdominal wall by means of a pump. At specific time intervals, the level of protein C in the blood was amidolytically determined. The following values were found:

| Time after administration (h) | Activity (U/ml) |
|---|---|
| 0 | 0 |
| 6 | 0.73 |
| 12 | 0.90 |
| 24 | 0.59 |
| 48 | 0.26 |

It is to be understood that the description, specific examples and data, while indicating preferred embodiments, are given by way of illustration and exemplification and are not intended to limit the present invention. Various changes and modifications within the present invention will become apparent to the skilled artisan from the discussion and disclosure contained herein.

We claim:

1. A method of administering protein C to a patient, comprising the step of:

subcutaneously injecting said patient with an agent comprising protein C and a pharmaceutically acceptable carrier.

2. A method according to claim 1, wherein said protein C is obtained from a natural source.

3. A method according to claim 1, wherein said protein C is obtained from a recombinant source.

4. A method according to claim 1, wherein said protein C is native protein C.

5. A method according to claim 1, wherein said protein C is in a zymogen form.

6. A method according to claim 1, wherein said protein C is in an activated form.

7. A method according to claim 1, wherein said protein C is at least 80% pure.

8. A method according to claim 1, wherein said protein C is at least 90% pure.

9. A method according to claim 1, wherein said protein C has been treated to inactivate or remove contaminating viruses.

10. A method of administering protein C to a patient, comprising the step of:

intramuscularly injecting said patient with an agent comprising protein C and a pharmaceutically acceptable carrier.

11. A method according to claim 10, wherein said protein C is obtained from a natural source.

12. A method according to claim 10, wherein said protein C is obtained from a recombinant source.

13. A method according to claim 10, wherein said protein C is native protein C.

14. A method according to claim 10, wherein said protein C is in a zymogen form.

15. A method according to claim 10, wherein said protein C is in an activated form.

16. A method according to claim 10, wherein said protein C is at least 80% pure.

17. A method according to claim 10, wherein said protein C is at least 90% pure.

18. A method according to claim 10, wherein said protein C has been treated to inactivate or remove contaminating viruses.

19. A method of treating a patient having protein C deficiency, comprising subcutaneously injecting into the patient a pharmaceutical agent comprising protein C.

20. The method according to claim 19, wherein protein C is native protein C.

21. The method according to claim 19, wherein the protein C is in an activated form.

22. The method according to claim 19, wherein the pharmaceutical agent further comprises a stabilizer and a pharmaceutically-acceptable carrier.

23. The method according to claim 22, wherein the stabilizer is selected from the group consisting of amino acids, sugars, tensides and polyalkylene glycols.

24. The method according to claim 19, wherein the pharmaceutical agent further comprises at least one protein selected from the group consisting of protein S and Factor V.

25. The method according to claim 19, wherein the protein C is injected at a dose of 200 to 1000 U/kg.

26. The method according to claim 19, wherein the protein C is in a prothrombin complex.

* * * * *